(12) United States Patent
Sakakibara et al.

(10) Patent No.: US 10,663,424 B2
(45) Date of Patent: May 26, 2020

(54) SENSOR ELEMENT AND GAS SENSOR (71) Applicant: NGK INSULATORS, LTD., Nagoya-shi, Aichi (JP)

(72) Inventors: Hironori Sakakibara, Nagoya (JP); Shuichi Ozawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 391 days.

(21) Appl. No.: 15/059,912

(22) Filed: Mar. 3, 2016

(65) Prior Publication Data
US 2016/0258897 A1 Sep. 8, 2016

(30) Foreign Application Priority Data

Mar. 6, 2015 (JP) .................. 2015-044293

(51) Int. Cl.
*G01N 27/407* (2006.01)
*G01N 27/419* (2006.01)
(Continued)

(52) U.S. Cl.
CPC ......... *G01N 27/4071* (2013.01); *G01N 27/41* (2013.01); *G01N 27/419* (2013.01); *G01N 33/0037* (2013.01); *Y02A 50/245* (2018.01)

(58) Field of Classification Search
CPC ........... G01N 27/4071; G01N 33/0037; G01N 27/419; G01N 33/0004–0075; G01N 27/406–41; Y02A 50/245
See application file for complete search history.

(56) References Cited

U.S. PATENT DOCUMENTS 5,997,707 A 12/1999 Kato et al.
2004/0069629 A1 4/2004 Tanaka et al.
(Continued)

FOREIGN PATENT DOCUMENTS

EP 2287599 A1 2/2011
EP 2312307 A1 4/2011
(Continued)

OTHER PUBLICATIONS

The Extended European Search Report for the corresponding European patent application No. 16158541.9 dated Jul. 18, 2016.
(Continued)

*Primary Examiner* — Maris R Kessel
*Assistant Examiner* — Joshua L Allen
(74) *Attorney, Agent, or Firm* — Global IP Counselors, LLP (57) ABSTRACT A sensor element includes a laminate, in which a plurality of oxygen ion-conductive solid electrolyte layers are stacked and in which a measurement object-gas flow portion is disposed, an inside pump electrode disposed on the inner circumferential surface of the measurement object-gas flow portion, an auxiliary pump electrode, and a measurement electrode. Then, the value of the volume ratio (Va=Vm/Vr) is 14.5 or more and 51.5 or less and the value of the volume ratio (Vb=Vs/Vr) is 5.0 or more and 17.5 or less, where the volume of the inside pump electrode 22 is specified as (Vm), the volume of the auxiliary pump electrode 51 is specified as (Vs), and the volume of the measurement electrode 44 is specified as (Vr).

9 Claims, 2 Drawing Sheets (51) Int. Cl.
*G01N 33/00* (2006.01)
*G01N 27/41* (2006.01)

(56) References Cited

U.S. PATENT DOCUMENTS

| | | | | |
|---|---|---|---|---|
| 2004/0217002 A1* | 11/2004 | Naito | ............ | G01N 27/4071 |
| | | | | 204/424 |
| 2010/0243444 A1 | 9/2010 | Wakazono et al. | | |
| 2011/0036715 A1* | 2/2011 | Horisaka | ............ | G01N 27/4071 |
| | | | | 204/424 |
| 2011/0147214 A1* | 6/2011 | Fujita | ............ | G01N 27/4071 |
| | | | | 204/424 |

FOREIGN PATENT DOCUMENTS

| | | | |
|---|---|---|---|
| JP | 9-318596 | A | 12/1997 |
| JP | 2004-93200 | A | 3/2004 |
| JP | 2004-132960 | A | 4/2004 |
| JP | 2007-33464 | A | 2/2007 |
| JP | 2010-249801 | A | 11/2010 |
| JP | 2011-038958 | A | 2/2011 |
| JP | 2011-102797 | A | 5/2011 |
| JP | 4911910 | B2 | 1/2012 |
| JP | 2014-190940 | A | 10/2014 |

OTHER PUBLICATIONS

Japanese Office Action dated Jun. 25, 2019 in corresponding Japanese Patent Application No. 2016-039851 (with English Translation).

* cited by examiner

FIG. 3 ered in the flow of the gas to be measured, a measurement electrode disposed on the inner circumferential surface of the measurement object-gas flow portion and disposed on the side downstream from the inside auxiliary pump electrode in the flow of the gas to be measured, and

SENSOR ELEMENT AND GAS SENSOR

BACKGROUND OF THE INVENTION

1. Field of the Invention

The present invention relates to a sensor element and a gas sensor.

2. Description of the Related Art

To date, gas sensors for detecting the concentrations of specific gases, e.g., NOx, in gases to be measured, such as automobile exhaust gases, are known. For example, PTL 1 and PTL 2 describe gas sensors including long lengths of plate-shaped sensor elements, in which a plurality of oxygen ion-conductive solid electrolyte layers are stacked. The sensor element includes a flow portion, which is disposed inside, of a gas to be measured, an outside pump electrode disposed outside the sensor element, an inside pump electrode and a measurement electrode disposed in the measurement object-gas flow portion, and a reference electrode, to which a reference gas serving as the reference of detection of a specific gas concentration is introduced.

Regarding such a sensor element, pumping in or pumping out of oxygen is performed between the inside of the measurement object-gas flow portion and the outside of the sensor element by a control voltage applied between the outside pump electrode and the inside pump electrode and, thereby, the oxygen concentration in the measurement object-gas flow portion is adjusted. Subsequently, the specific gas in the gas to be measured after adjustment of the oxygen concentration is reduced, and the specific gas concentration in the gas to be measured is detected on the basis of a current which flows between the outside pump electrode and a measurement electrode in accordance with the oxygen concentration after the reduction. In this regard, feedback control is used for adjusting the oxygen concentration in the measurement object-gas flow portion. Specifically, the oxygen concentration in the measurement object-gas flow portion is determined by measuring the electromotive force between the inside pump electrode and the reference electrode. The control voltage is feedback-controlled so as to make the electromotive force constant.

CITATION LIST

Patent Literature

[PTL 1] JP 2014-190940 A
[PTL 2] JP 2011-102797 A

SUMMARY OF THE INVENTION

In the case where such feedback control is performed, it is preferable that controllability (responsiveness and stability) be high. As the controllability becomes high, the detection accuracy of the specific gas concentration in the gas to be measured tends to be improved. Consequently, it is desirable that the controllability be improved.

The present invention was made so as to solve such problems and a main object is to improve the controllability of feedback control using a sensor element.

In the present invention, the following measures are adopted so as to achieve the above-described main object.

A sensor element according to the present invention includes a laminate, in which a plurality of oxygen ion-conductive solid electrolyte layers are stacked and in which a measurement object-gas flow portion is disposed so as to introduce the gas to be measured from the outside, an outside pump electrode disposed on the outside surface of the laminate, an inside main pump electrode disposed on the inner circumferential surface of the measurement object-gas flow portion, an inside auxiliary pump electrode disposed on the inner circumferential surface of the measurement object-gas flow portion and disposed on the side downstream from the inside main pump electrode in the flow of the gas to be measured, a measurement electrode disposed on the inner circumferential surface of the measurement object-gas flow portion and disposed on the side downstream from the inside auxiliary pump electrode in the flow of the gas to be measured, and a reference electrode which is disposed in the laminate and to which a reference gas serving as the reference of detection of a specific gas concentration in the gas to be measured is introduced, wherein the value of the volume ratio VA (=Vm/Vr) is 14.5 or more and 51.5 or less and the value of the volume ratio Vb (=Vs/Vr) is 5.0 or more and 17.5 or less, where the volume of the inside main pump electrode is specified as Vm, the volume of the inside auxiliary pump electrode is specified as Vs, and the volume of the measurement electrode is specified as Vt.

Regarding this sensor element, the value of the volume ratio Va (=Vm/Vr), which is the ratio of the volume Vm of the inside main pump electrode to the volume Vr of the measurement electrode, is 14.5 or more and, thereby, degradation of the responsiveness of feedback control using the inside main pump electrode is suppressed. The value of the volume ratio Va is 51.5 or less and, thereby, degradation of the stability of feedback control using the inside main pump electrode is suppressed. Also, the value of the volume ratio Vb (=Vs/Vr), which is the ratio of the volume Vs of the inside auxiliary pump electrode to the volume Vr of the measurement electrode is 5.0 or more and, thereby, degradation of the responsiveness of feedback control using the inside auxiliary pump electrode can be suppressed. The value of the volume ratio Vb is 17.5 or less and, thereby, degradation of the stability of feedback control using the inside auxiliary pump electrode can be suppressed. Consequently, the controllability (responsiveness and stability) of feedback control is improved.

In the sensor element according to the present invention, the value of the volume ratio Va may be 22.5 or more and 35.0 or less. The controllability of feedback control is thereby further improved.

In the sensor element according to the present invention, the value of the volume ratio Vb may be 8.0 or more and 12.0 or less. The controllability of feedback control is thereby further improved.

In the sensor element according to the present invention, the value of the volume ratio Vc (=Vm/Vs) may be 1.0 or more and 7.0 or less. The controllability of feedback control is thereby further improved. The value of the volume ratio Vc is preferably 2.0 or more. The value of the volume ratio Vc is preferably 4.0 or less. The value of the volume ratio Vc may be 3.0 or less.

In the sensor element according to the present invention, the laminate may have the measurement object-gas flow portion, in which a first internal space and a second internal space are disposed in that order from an inlet of the gas to be measured along the introduction direction, the inside main pump electrode may be disposed on the inner circumferential surface of the first internal space, the inside auxiliary pump electrode may be disposed on the inner circumferential surface of the second internal space, and a main pump cell which is configured to include the outside pump electrode, the inside main pump electrode, and the solid electrolyte layer between the outside pump electrode and the inside main pump electrode in the laminate and which performs pumping in or pumping out of oxygen of the first internal space, an auxiliary pump cell which is configured to include the outside pump electrode, the inside auxiliary pump electrode, and the solid electrolyte layer between the outside pump electrode and the inside auxiliary pump electrode in the laminate and which performs pumping in or pumping out of oxygen of the second internal space, and a measurement pump cell which is configured to include the outside pump electrode, the measurement electrode, and the solid electrolyte layer between the outside pump electrode and the measurement electrode in the laminate and which performs pumping in or pumping out of oxygen around the measurement electrode may be included.

A gas sensor according to the present invention includes the sensor element of the present invention according to any one of the above-described aspects. Consequently, with the gas sensor of the present invention, the same effects as those of the above-described sensor element according to the present invention, for example, the effect of improving the controllability of feedback control, are obtained.

DETAILED DESCRIPTION OF THE INVENTION

Figure 1:
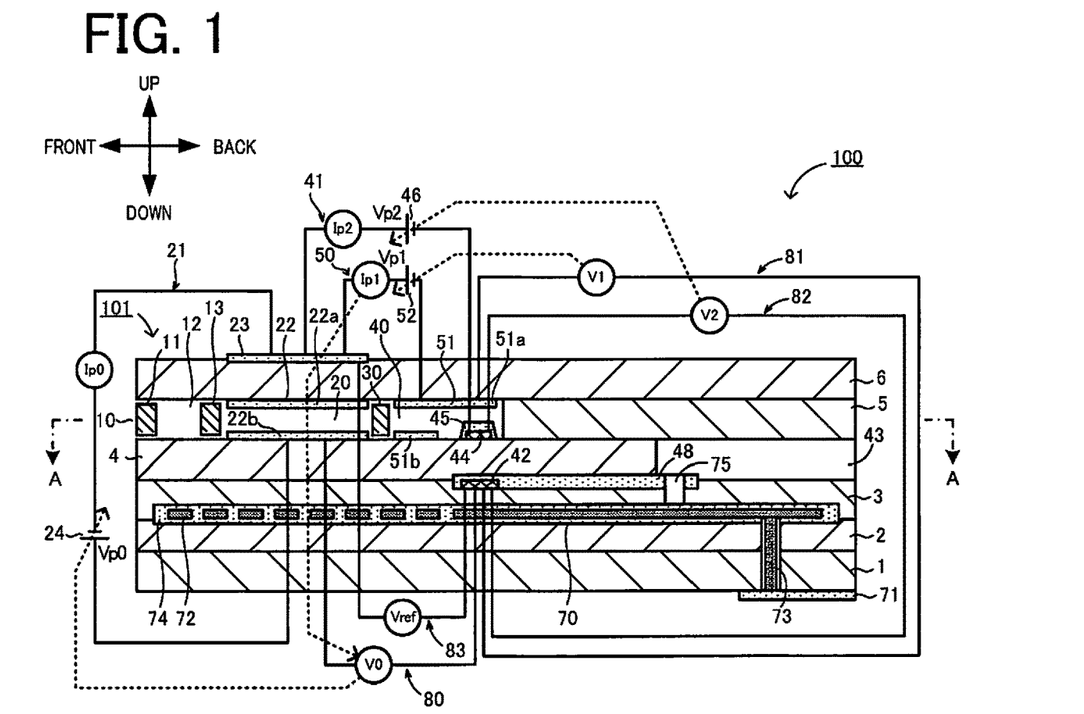
FIG. 1 is a schematic sectional view showing an outline of an example of the configuration of a gas sensor 100.
Figure 2:
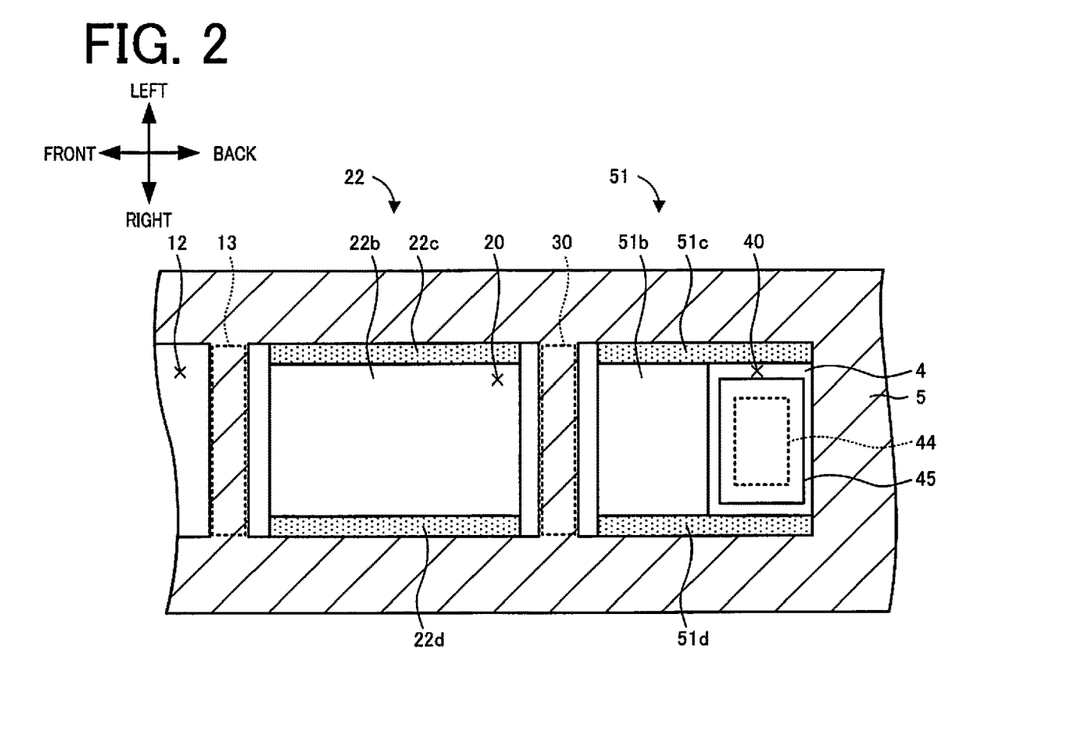
FIG. 2 is a cross-section (partial sectional view) along a line A-A shown in FIG. 1

Next, embodiments according to the present invention will be described with reference to the drawings. FIG. 1 is a schematic sectional view showing an outline of an example of the configuration of a gas sensor 100 according to an embodiment of the present invention. FIG. 2 is a partial sectional view showing a first internal space 20 and a second internal space 40 and the periphery thereof in a cross-section along a line A-A shown in FIG. 1. The gas sensor 100 includes a sensor element 101 for detecting the concentration of a specific gas (NOx in the present embodiment) in a gas to be measured. The sensor element 101 has long lengths of rectangular parallelepiped shape. The longitudinal direction of the sensor element 101 (lateral direction in FIG. 1) is specified as a forward or backward direction and the thickness direction of the sensor element 101 (vertical direction in FIG. 1) is specified as a vertical direction. Also, the width direction of the sensor element 101 (direction perpendicular to the forward or backward direction and the vertical direction) is specified as a lateral direction.

The sensor element 101 is an element having a layered structure in which six layers composed of a first substrate layer 1, a second substrate layer 2, a third substrate layer 3, a first solid electrolyte layer 4, a spacer layer 5, and a second solid electrolyte layer 6, each being formed from an oxygen ion-conductive solid electrolyte layer of zirconia ($ZrO_2$) or the like, are stacked in that order from the bottom side. Also, the solid electrolyte constituting these six layers is dense and airtight. The above-described sensor element 101 is produced by, for example, subjecting ceramic green sheets corresponding to the individual layers to predetermined processing, printing of circuit patterns, and the like, stacking them thereafter, and further performing firing so as to integrate the ceramic green sheets.

In one end portion (front end portion) of the sensor element 101 and between the lower surface of the second solid electrolyte layer 6 and the upper surface of the first solid electrolyte layer 4, a gas inlet 10, a first diffusion-controlled portion 11, a buffer space 12, a second diffusion-controlled portion 13, a first internal space 20, a third diffusion-controlled portion 30, and a second internal space 40 are formed in that order so as to adjoin and communicate.

The gas inlet 10, the buffer space 12, the first internal space 20, and the second internal space 40 are spaces in the inside of the sensor element 101 by hollowing the spacer layer 5, where the upper portion is defined by the lower surface of the second solid electrolyte layer 6, the lower portion is defined by the upper surface of the first solid electrolyte layer 4, and the side portions are defined by the side surfaces of the spacer layer 5.

Each of the first diffusion-controlled portion 11, the second diffusion-controlled portion 13, and the third diffusion-controlled portion 30 is provided as two horizontally oriented (the longitudinal direction of the opening is a direction perpendicular to FIG. 1) slits. In this regard, the portions from the gas inlet 10 to the second internal space 40 may be referred to as a measurement object-gas flow portion.

Meanwhile, at the position farther from the front end side than the measurement object-gas flow portion, a reference gas introduction space 43 is provided at the location between the upper surface of the third substrate layer 3 and the lower surface of the spacer layer 5, where the side portions are defined by the side surfaces of the first solid electrolyte layer 4. For example, the air serving as the reference gas at the time of measurement of the NOx concentration is introduced into the reference gas introduction space 43.

An air introduction layer 48 is a layer composed of porous ceramics. The reference gas is introduced into the air introduction layer 48 through the gas introduction space 43. Also, the air introduction layer 48 is formed so as to cover a reference electrode 42.

The reference electrode 42 is an electrode formed so as to be sandwiched between the upper surface of the third substrate layer 3 and the first solid electrolyte layer 4 and, as described above, the air introduction layer 48 connected to the reference gas introduction space 43 is disposed around the reference electrode 42. In this regard, the reference electrode 42 is formed directly on the upper surface of the third substrate layer 3 and the portion other than the portion in contact with the upper surface of the third substrate layer 3 is covered with the air introduction layer 48. In addition, as described later, it is possible to measure the oxygen concentrations (oxygen partial pressures) in the first internal space 20 and the second internal space 40 by using the reference electrode 42.

In the measurement object-gas flow portion, the gas inlet 10 is a part made open to the outside space, and the gas to be measured is taken from the outside space into the sensor element 101 through the gas inlet 10. The first diffusion-controlled portion 11 is a part for giving predetermined diffusion resistance to the gas to be measured, where the gas is taken from the gas inlet 10. The buffer space 12 is a space provided so as to lead the gas to be measured, where the gas is introduced from the first diffusion-controlled portion 11, to the second diffusion-controlled portion 13. The second diffusion-controlled portion 13 is a part for giving predetermined diffusion resistance to the gas to be measured, where the gas is introduced from the buffer space 12 to the first internal space 20. When the gas to be measured is introduced from the outside of the sensor element 101 into the first internal space 20, the gas to be measured, which is taken into the sensor element 101 through the gas inlet 10 rapidly because of the pressure fluctuation of the gas to be measured in the outside space (pulsation of an exhaust pressure in the case where the gas to be measured is an automotive exhaust gas), is not directly introduced into the first internal space 20 but introduced into the first internal space 20 after concentration variations of the gas to be measured are canceled through the first diffusion-controlled portion 11, the buffer space 12, and the second diffusion-controlled portion 13. Consequently, concentration variations of the gas to be measured, which is introduced into the first internal space 20, are made to be at an almost negligible level. The first internal space 20 is provided as a space for adjusting the oxygen partial pressure in the gas to be measured which is introduced through the second diffusion-controlled portion 13. The above-described oxygen partial pressure is adjusted by actuation of a main pump cell 21.

The main pump cell 21 is an electrochemical pump cell constructed by an inside pump electrode 22 having a ceiling electrode portion 22a provided on an almost entire surface of the lower surface of the second solid electrolyte layer 6 facing the first internal space 20, an outside pump electrode 23 provided in a region, which corresponds to the ceiling electrode portion 22a, on the upper surface of the second solid electrolyte layer 6 so as to be exposed to the outside space, and the second solid electrolyte layer 6 sandwiched between these electrodes.

The inside pump electrode 22 is formed so as to extend over the upper and lower solid electrolyte layers (second solid electrolyte layer 6 and first solid electrolyte layer 4) demarcating the first internal space 20 and the spacer layer 5 providing the side walls. Specifically, the ceiling electrode portion 22a is formed on the lower surface of the second solid electrolyte layer 6 providing the ceiling surface of the first internal space 20 and a bottom electrode portion 22b is formed on the upper surface of the first solid electrolyte layer 4 providing the bottom surface. Also, side electrode portions 22c and 22d (refer to FIG. 2) for connecting the ceiling electrode portion 22a to the bottom electrode portion 22b are formed on both the left and right wall surfaces, respectively, of the spacer layer 5 providing side walls of the first internal space 20. Consequently, the inside pump electrode 22 has a tunnel form structure including the ceiling electrode portion 22a, the bottom electrode portion 22b, and the side electrode portions 22c and 22d. In the present embodiment, the locations of formation and the shapes of the ceiling electrode portion 22a and the bottom electrode portion 22b are symmetric with respect to a horizontal line. Also, the locations of formation and the shapes of the side electrode portion 22c and the side electrode portion 22d are symmetric with respect to a vertical line. However, the configuration is not limited to them. The ceiling electrode portion 22a and the bottom electrode portion 22b may be asymmetric. The side electrode portion 22c and the side electrode portion 22d may be asymmetric. The side electrode portions 22c and 22d need only to electrically connect the ceiling electrode portion 22a to the bottom electrode portion 22b.

The inside pump electrode 22 and the outside pump electrode 23 are formed as porous cermet electrodes (for example, a cermet electrode of Pt containing 1% of Au and $ZrO_2$). In this regard, the inside pump electrode 22 to contact with the gas to be measured is formed by using a material having weakened ability to reduce NOx components in the gas to be measured.

In the main pump cell 21, oxygen in the first internal space 20 can be pumped out to the outside space or oxygen in the outside space can be pumped into the first internal space 20 by applying a predetermined pump voltage Vp0 between the inside pump electrode 22 and the outside pump electrode 23 and passing a pump current Ip0 between the inside pump electrode 22 and the outside pump electrode 23 in the positive direction or negative direction.

In addition, in order to detect the oxygen concentration (oxygen partial pressure) in the atmosphere in the first internal space 20, an electrochemical sensor cell, that is, a main pump controlling oxygen partial pressure detection sensor cell 80 is constructed by the inside pump electrode 22, the second solid electrolyte layer 6, the spacer layer 5, the first solid electrolyte layer 4, the third substrate layer 3, and the reference electrode 42.

The oxygen concentration (oxygen partial pressure) in the first internal space 20 is determined by measuring the electromotive force V0 of the main pump controlling oxygen partial pressure detection sensor cell 80. Further, the pump current Ip0 is controlled by feedback-controlling the pump voltage Vp0 of a variable power supply 24 so as to make the electromotive force V0 reach (approach) a predetermined target value V0*. Consequently, the oxygen concentration in the first internal space 20 can be maintained at a predetermined constant value.

The third diffusion-controlled portion 30 is a part which gives predetermined diffusion resistance to the gas to be measured, the oxygen concentration (oxygen partial pressure) of the gas having been controlled by the operation of the main pump cell 21 in the first internal space 20, and leads the gas to be measured into the second internal space 40.

The second internal space 40 is provided as a space for performing a treatment related to the measurement of the nitrogen oxide (NOx) concentration in the gas to be measured that is introduced through the third diffusion-controlled portion 30. The NOx concentration is measured mainly in the second internal space 40 in which the oxygen concentration is adjusted by an auxiliary pump cell 50 and further the NOx concentration is measured by the operation of a measurement pump cell 41.

In the second internal space 40, the gas to be measured is further subjected to adjustment of the oxygen partial pressure by the auxiliary pump cell 50, the gas to be measured having been subjected to adjustment of the oxygen concentration (oxygen partial pressure) in the first internal space 20 in advance and, thereafter, having been introduced through the third diffusion-controlled portion 30. Consequently, the oxygen concentration in the second internal space 40 can be maintained constant with high accuracy and, therefore, the gas sensor 100 can measure the NOx concentration with high accuracy.

The auxiliary pump cell 50 is an auxiliary electrochemical pump cell constructed by an auxiliary pump electrode 51 having a ceiling electrode portion 51a disposed on almost entire surface of the lower surface of the second solid electrolyte layer 6 facing the second internal space 40, an outside pump electrode 23 (not limited to the outside pump electrode 23, and an appropriate electrode outside the sensor element 101 will suffice), and the second solid electrolyte layer 6.

The above-described auxiliary pump electrode 51 is arranged in the second internal space 40 so as to have the same tunnel form structure as the above-described inside pump electrode 22 disposed in the first internal space 20. That is, the ceiling electrode portion 51a is formed on the lower surface of the second solid electrolyte layer 6 providing the ceiling surface of the second internal space 40, and a bottom electrode portion 51b is formed on the upper surface of the first solid electrolyte layer 4 providing the bottom surface of the second internal space 40. Also, side electrode portions 51c and 51d (refer to FIG. 2) for connecting the ceiling electrode portion 51a to the bottom electrode portion 51b are formed on both the left and right wall surfaces, respectively, of the spacer layer 5 providing side walls of the second internal space 40. Consequently, the auxiliary pump electrode 51 has a tunnel form structure including the ceiling electrode portion 51a, the bottom electrode portion 51b, and the side electrode portions 51c and 51d. In the present embodiment, the locations of formation and the shapes of the side electrode portion 51c and the side electrode portion 51d are symmetric with respect to a vertical line. However, the configuration is not limited to them. The side electrode portions 51c and 51d need only to electrically connect the ceiling electrode portion 51a to the bottom electrode portion 51b. In this regard, the auxiliary pump electrode 51 is formed by using a material having weakened ability to reduce NOx components in the gas to be measured in the same manner as the inside pump electrode 22.

In the auxiliary pump cell 50, oxygen in the atmosphere in the second internal space 40 can be pumped out to the outside space or oxygen in the outside space can be pumped into the second internal space 40 by applying a predetermined pump voltage Vp1 to between the auxiliary pump electrode 51 and the outside pump electrode 23.

In addition, in order to control the oxygen partial pressure in the atmosphere in the second internal space 40, an electrochemical sensor cell, that is, an oxygen partial pressure detection sensor cell 81 for controlling the auxiliary pump is constructed by the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 performs pumping by using a variable power supply 52 which is voltage-controlled on the basis of the electromotive force V1 detected by the oxygen partial pressure detection sensor cell 81 for controlling the auxiliary pump. Specifically, the pump current Ip1 of the auxiliary pump cell 50 is controlled by feedback-controlling the pump voltage Vp1 of the variable power supply 52 so as to make the electromotive force V1 reach (approach) a predetermined target value V1*. Consequently, the oxygen partial pressure in the atmosphere in the second internal space 40 is reduced to a low partial pressure that does not substantially affect the measurement of NOx.

In addition to this, the pump current Ip1 is used for controlling the electromotive force of the oxygen partial pressure detection sensor cell 80 for controlling the main pump. Specifically, the pump current Ip1 serving as a control signal is input into the oxygen partial pressure detection sensor cell 80 for controlling the main pump, and the electromotive force V0 is controlled. More specifically, a target value V0* of the electromotive force V0 when feedback-controlling the above-described voltage V0 is determined on the basis of the value of the pump current Ip1. Consequently, the gradient of the oxygen partial pressure in the gas to be measured, which is introduced from the third diffusion-controlled portion 30 into the second internal space 40, is controlled so as to become always constant. In the case of application as a NOx sensor, the oxygen concentration in the second internal space 40 is maintained at a constant value of about 0.001 ppm by the functions of the main pump cell 21 and the auxiliary pump cell 50.

The measurement pump cell 41 measures the NOx concentration in the gas to be measured in the second internal space 40. The measurement pump cell 41 is an electrochemical pump cell constructed by a measurement electrode 44 disposed on the upper surface of the first solid electrolyte layer 4 facing the second internal space 40 and at the position apart from the third diffusion-controlled portion 30, the outside pump electrode 23, the second solid electrolyte layer 6, the spacer layer 5, and the first solid electrolyte layer 4.

The measurement electrode 44 is a porous cermet electrode. The measurement electrode 44 also functions as a reduction catalyst for reducing a specific gas (NOx in the present invention) present in the atmosphere in the second internal space 40. Further, the measurement electrode 44 is covered with a fourth diffusion-controlled portion 45. The measurement electrode 44 is a porous cermet electrode composed of Pt containing 1% of Au, a platinum group element having catalytic activity, and $ZrO_2$. Examples of platinum group elements include ruthenium, rhodium, palladium, osmium, and iridium.

The fourth diffusion-controlled portion 45 is a film composed of a ceramic porous body. The fourth diffusion-controlled portion 45 has a function of restricting the amount of NOx flowing into the measurement electrode 44 and, in addition, a function as a protective film for the measurement electrode 44. In the measurement pump cell 41, oxygen generated by decomposition of nitrogen oxides in the atmosphere around the measurement electrode 44 is pumped out and the amount of generation thereof can be detected as a pump current Ip2.

Also, in order to detect the oxygen partial pressure around the measurement electrode 44, an electrochemical sensor cell, that is, a measurement pump controlling oxygen partial pressure detection sensor cell 82 is constructed by the first solid electrolyte layer 4, the third substrate layer 3, the measurement electrode 44, and the reference electrode 42. A variable power supply 46 is controlled on the basis of the electromotive force V2 detected by the measurement pump controlling oxygen partial pressure detection sensor cell 82.

The gas to be measured, which is introduced into the second internal space 40, reaches the measurement electrode 44 through the fourth diffusion-controlled portion 45 under circumstances where the oxygen partial pressure is controlled. Nitrogen oxides in the gas to be measured around the measurement electrode 44 are reduced ($2NO \rightarrow N_2+O_2$) and oxygen is generated. Then, the resulting oxygen is pumped by the measurement pump cell 41. At that time, the voltage Vp2 of the variable power supply 46 is feedback-controlled so as to make the electromotive force V2 detected by the measurement pump controlling oxygen partial pressure detection sensor cell 82 reach (approach) a predetermined target value V2*. The amount of oxygen generated around the measurement electrode 44 is proportional to the concentration of the nitrogen oxides in the gas to be measured and, therefore, the nitrogen oxide concentration in the gas to be measured is calculated by using the pump current Ip2 in the measurement pump cell 41.

In addition, in the case where the measurement electrode 44, the first solid electrolyte layer 4, the third substrate layer 3, and the reference electrode 42 are combined so as to constitute an oxygen partial pressure detection device as an electrochemical sensor cell, the electromotive force in accordance with the difference between the amount of oxygen generated by reduction of NOx components in the atmosphere around the measurement electrode 44 and the amount of oxygen contained in the reference air can be detected and, thereby, the concentration of NOx components in the gas to be measured can be determined.

Further, an electrochemical sensor cell 83 is constructed by the second solid electrolyte layer 6, the spacer layer 5, the first solid electrolyte layer 4, the third substrate layer 3, the outside pump electrode 23, and the reference electrode 42. The oxygen partial pressure in the gas to be measured in the outside of the sensor can be detected by the electromotive force Vref obtained by the sensor cell 83.

In the gas sensor 100 having the above-described configuration, the gas to be measured, which has an oxygen partial pressure always maintained at a low constant value (value that does not substantially affect the measurement of NOx) by actuation of the main pump cell 21 and the auxiliary pump cell 50, is fed to the measurement pump cell 41. Therefore, the NOx concentration in the gas to be measured can be determined on the basis of the pump current Ip2 that flows because oxygen, which is generated by reduction of NOx nearly in proportion to the NOx concentration in the gas to be measured, is pumped out of the measurement pump cell 41.

Further, in order to enhance the oxygen ion conductivity of the solid electrolyte, the sensor element 101 includes a heater portion 70 having a function of adjusting the temperature including heating the sensor element 101 and keeping the temperature. The heater portion 70 includes a heater connector electrode 71, a heater 72, a through hole 73, a heater insulating layer 74, and a pressure release hole 75.

The heater connector electrode 71 is an electrode formed so as to contact with the lower surface of the first substrate layer 1. The electric power can be supplied from the outside to the heater portion 70 by connecting the heater connector electrode 71 to an external power supply.

The heater 72 is an electric resistor formed to be sandwiched between the second substrate layer 2 and the third substrate layer 3 in the vertical direction. The heater 72 is connected to the heater connector electrode 71 through the through hole 73 and generates heat by being supplied with an electric power from the outside through the heater connector electrode 71 so as to heat the solid electrolyte constituting the sensor element 101 and keep the temperature.

Also, the heater 72 is embedded over an entire range from the first internal space 20 to the second internal space 40 and the entirety of the sensor element 101 can be adjusted to have a temperature at which the above-described solid electrolyte is activated.

The heater insulating layer 74 is an insulating layer formed on the upper and lower surfaces of the heater 72 by using an insulator, e.g., alumina. The heater insulating layer 74 is formed for the purpose of establishing electrical insulation between the second substrate layer 2 and the heater 72 and electrical insulation between the third substrate layer 3 and the heater 72.

The pressure release hole 75 is a part provided so as to penetrate the third substrate layer 3 and communicate with the reference gas introduction space 43 and is formed for the purpose of reducing an internal pressure increase associated with a temperature increase in the heater insulating layer 74.

A plurality of connector electrodes (connector pads), although not shown in the drawing, are disposed on the rear end side of the upper surface of the second solid electrolyte layer 6 and on the rear end side of the lower surface of the first substrate layer 1. Voltages or currents can be applied to the individual electrodes (inside pump electrode 22, outside pump electrode 23, reference electrode 42, measurement electrode 44, and auxiliary pump electrode 51) of the sensor element 101 or the voltages and the currents of the individual electrodes can be measured from the outside through these connector electrodes. Application of the voltage by the above-described variable power supply 24, variable power supply 46, or variable power supply 52, detection of pump currents Ip1 and Ip2 and electromotive forces V0, V1, and V2, and the like are performed through the individual connector electrodes in practice.

Here, the inside pump electrode 22, the auxiliary pump electrode 51, and the measurement electrode 44 will be described in detail. In the present embodiment, the value of the volume ratio Va (=Vm/Vr) is 14.5 or more and 51.5 or less and the value of the volume ratio Vb (=Vs/Vr) is 5.0 or more and 17.5 or less, where the volume of the inside pump electrode 22 is specified as Vm, the volume of the auxiliary pump electrode 51 is specified as Vs, and the volume of the measurement electrode 44 is specified as Vr. If the value of the volume ratio Va is 14.5 or more, degradation of the responsiveness of feedback control using the inside pump electrode 22 is suppressed. If the value of the volume ratio Va is 51.5 or less, degradation of the stability of feedback control using the inside pump electrode 22 is suppressed. Also, if the value of the volume ratio Vb is 5.0 or more, degradation of the responsiveness of feedback control using the auxiliary pump electrode 51 can be suppressed. If the value of the volume ratio Vb is 17.5 or less, degradation of the stability of feedback control using the auxiliary pump electrode 51 can be suppressed. The reasons for this will be described below.

To begin with, an example of application of the sensor element 101 according to the present invention using the feedback control will be collectively described again below. As described above, the pump voltage Vp0 applied between the outside pump electrode 23 and the inside pump electrode 22 is feedback-controlled so as to make the electromotive force V0 between the inside pump electrode 22 and the reference electrode 42 reach the predetermined target value V0*, the pump current Ip0 is controlled by the pump voltage Vp0 and, thereby, pumping out or pumping in of oxygen in the measurement object-gas flow portion is performed. Consequently, the concentration of oxygen, which is introduced from the outside into the measurement object-gas flow portion, in the gas to be measured in the first internal space 20 is adjusted. Also, the pump voltage Vp1 applied between the outside pump electrode 23 and the auxiliary pump electrode 51 is feedback-controlled so as to make the electromotive force V1 between the auxiliary pump electrode 51 and the reference electrode 42 reach the predetermined target value V1*, the pump current Ip1 is controlled by the pump voltage Vp1 and, thereby, pumping out or pumping in of oxygen in the measurement object-gas flow portion is performed. Consequently, the oxygen concentration that has been adjusted in the first internal space 20 in the gas to be measured is further adjusted by using the auxiliary pump electrode 51 in the second internal space 40. As a result, the gas to be measured, which has an oxygen concentration adjusted while passing through the first internal space 20 and the second internal space 40, passes through the fourth diffusion-controlled portion 45 and arrives in the vicinity of the measurement electrode 44. In addition, a target value V0* of the electromotive force V0 when feedback-controlling the voltage V0 is determined on the basis of the value of the pump current Ip1. Consequently, the gradient of the oxygen partial pressure in the gas to be measured, which is introduced from the third diffusion-controlled portion 30 into the second internal space 40, is controlled so as to become always constant and the oxygen concentration in the second internal space 40 is maintained more accurately. Then, the specific gas (NOx) in the resulting gas to be measured is reduced by the measurement electrode 44, and an electromotive force V2 is generated between the measurement electrode 44 and the reference electrode 42 in accordance with the oxygen concentration after reduction. Subsequently, the specific gas (NOx) concentration in the gas to be measured is calculated by using the resulting electromotive force V2. Alternatively, the pump voltage Vp2 is feedback-controlled so as to make the electromotive force V2 reach the predetermined target value V2*, and the specific gas (NOx) concentration in the gas to be measured is calculated by using the current Ip2 made to flow by the voltage Vp2.

In the case where such feedback control is used, as the volume Vm of the inside pump electrode 22 increases, the reactivity of oxygen (reduction reaction from an oxygen molecule to an oxygen ion or oxidation reaction from an oxygen ion to an oxygen molecule) at the inside pump electrode 22 tends to be enhanced. Consequently, as the volume Vm increases, the electromotive force V0 between the inside pump electrode 22 and the reference electrode 42 is changed easily, and the stability of control is degraded easily in the case where feedback control is performed so as to make the electromotive force V0 reach the target value V0*. For example, the value of the electromotive force V0 overshoots the target value V0* easily, and by extension the oxygen concentration in the first internal space 20 overshoots the target value easily. For the same reason, as the volume Vm decreases, the electromotive force V0 is not changed easily, and the responsiveness of control is degraded easily in the case where feedback control is performed so as to make the electromotive force V0 reach the target value V0*. For example, the time period until the value of the electromotive force V0 reaches the target value V0* increases easily, and by extension the time period until the oxygen concentration in the first internal space 20 reaches the target value increases easily. The same goes for the volume Vs of the auxiliary pump electrode 51. As the volume Vs increases, the electromotive force V1 is changed easily, and the stability of control is degraded easily in the case where feedback control is performed so as to make the electromotive force V1 reach the target value V1*. Consequently, for example, the oxygen concentration in the second internal space 40 overshoots the target value easily. As the volume Vs decreases, the electromotive force V1 is not changed easily, and the responsiveness of control is degraded easily in the case where feedback control is performed so as to make the electromotive force V1 reach the target value V1*. Consequently, for example, the time period until the oxygen concentration in the second internal space 40 reaches the target value increases easily. Meanwhile, the adjustment of the oxygen concentration in the second internal space 40 by using the auxiliary pump electrode 51 is performed with respect to the gas to be measured after subjected to adjustment of the oxygen concentration in the first internal space 20 by using the inside pump electrode 22. Therefore, the quality of the controllability of feedback control using the inside pump electrode 22 has an influence on the quality of the controllability of feedback control using the auxiliary pump electrode 51. In addition, in the present embodiment, the target value V0* is determined based on the value of the pump current Ip1. Consequently, the quality of the controllability of feedback control using the auxiliary pump electrode 51 has an influence on the quality of the controllability of feedback control using the inside pump electrode 22. That is, the quality of the controllability of feedback control using the inside pump electrode 22 and the quality of the controllability of feedback control using the auxiliary pump electrode 51 have influence on each other and are connected with each other. Therefore, in order to improve both the controllability of feedback control using the inside pump electrode 22 and the controllability of feedback control using the auxiliary pump electrode 51, both the volume Vm and the volume Vs have to be adjusted to preferable values. Meanwhile, detection of the specific gas (MO concentration by using the measurement electrode 44 is performed with respect to the gas to be measured after subjected to adjustment of the oxygen concentration in the second internal space 40 by using the auxiliary pump electrode 51. Consequently, the quality of the controllability of feedback control using the auxiliary pump electrode 51 also has an effect on the detection accuracy of the specific gas concentration by using the measurement electrode 44 (specifically the value of the electromotive force V2 and the value of the current Ip2 based on V2). Therefore, it is considered that preferable ranges of the volume Vm and the Volume Vs are changed depending on the volume Vr of the measurement electrode as well. As a result, it is considered that in the sensor element 101 according to the present embodiment, the controllability (responsiveness and stability) of feedback control is improved by specifying the value of the volume ratio Va as 14.5 or more and 51.5 or less and the value of the volume Vb as 5.0 or more and 17.5 or less, where the volume Va (=Vm/Vr) and the volume Vb (=Vs/Vr) are defined as values representing the volume Vm and the Volume Vs with reference to the volume Vr of the measurement electrode. Then, the detection accuracy of the specific gas concentration by using the measurement electrode 44 is improved because the controllability of feedback control is improved.

In this regard, the value of the volume ratio Va is preferably 17. 5 or more, the value is more preferably 22.5 or more, and the value is further preferably 23.5 or more because degradation of the responsiveness of feedback control using the inside pump electrode 22 can be further suppressed. The value of the volume ratio Va is preferably 48.0 or less, the value is more preferably 35.0 or less, and the value is further preferably 30.5 or less because degradation of the stability of feedback control using the inside pump electrode 22 can be further suppressed. The value of the volume ratio Vb is preferably 6.0 or more and the value is more preferably 8.0 or more because degradation of the responsiveness of feedback control using the auxiliary pump electrode 51 can be further suppressed. The value of the volume ratio Vb is preferably 16.5 or less, the value is more preferably 12.0 or less, and the value is further preferably 10.5 or less because degradation of the stability of feedback control using the auxiliary pump electrode 51 can be further suppressed. Also, the value of the volume ratio Vc (=Vm/Vs), which is the value representing the volume Vm with reference to the volume Vs, is preferably 1.0 or more and 7.0 or less because the controllability of feedback control is further improved. The value of the volume ratio Vc is more preferably 2.0 or more. The value of the volume ratio Vc is more preferably 4.0 or less. The value of the volume ratio Vc may be 3.0 or less. In this regard, the volume Vm is a total of the volumes of the ceiling electrode portion 22a, the bottom electrode portion 22b, and the side electrode portions 22c and 22d. The volume Vs is a total of the volumes of the ceiling electrode portion 51a, the bottom electrode portion 51b, and the side electrode portions 51c and Sld. The volume Vm is, for example, 0.3 mm$^3$ to 2.0 mm$^3$, the volume Vs is, for example, 0.1 mm$^3$ to 0.6 mm$^3$, and the volume Vr is, for example, 0.01 mm$^3$ to 0.03 mm$^3$, although not specifically limited to these.

Next, the method for manufacturing the above-described gas sensor 100 will be described. Initially, six unfired ceramic green sheets containing oxygen ion-conductive solid electrolyte, e.g., zirconia, as a ceramic component are prepared. A plurality of sheet holes used for positioning when printing or stacking is performed, necessary through holes, and the like are formed in these green sheets in advance. Also, a space serving as the measurement object-gas flow portion is disposed in a green sheet serving as a spacer layer 5 in advance by punching or the like. Likewise, a space serving as the reference gas introduction space 43 is disposed in a green sheet serving as the first solid electrolyte layer 4. Then, pattern printing and drying are performed, where various patterns are formed on the individual ceramic green sheets in accordance with each of the first substrate layer 1, the second substrate layer 2, the third substrate layer 3, the first solid electrolyte layer 4, the spacer layer 5, and the second solid electrolyte layer 6. Specific examples of the pattern formed include patterns of the above-described individual electrodes, individual insulating layers, and heater portion 70. The pattern printing is performed by coating the green sheets with pattern-forming pastes prepared in accordance with the characteristics required of the individual subjects of formation on the basis of a known screen printing technology. An electrically conductive paste is used as the pattern-forming paste of each electrode. Regarding the patterns of the electrically conductive pastes serving as the inside pump electrode 22, the auxiliary pump electrode 51, and the measurement electrode 44, the individual pattern shapes, coating areas, coating thickness (viscosity of the electrically conductive paste), and the like are set appropriately so as to make the above-described volume ratios Va, Vb, and Vc take on predetermined values. The drying is performed by using a known drying device. After the pattern printing and the drying are finished, printing and drying of a bonding paste are performed in order to stack and bond the green sheets corresponding to the individual layers to one another. Subsequently, the green sheets provided with the bonding paste are positioned on the basis of the sheet holes and are stacked in a predetermined order. Contact bonding is performed, where one laminate is produced by contact bonding under predetermined temperature and pressure conditions. The thus obtained laminate includes a plurality of sensor elements 101. The laminate is divided into the size of the sensor element 101 by cutting. The resulting laminate is fired at a predetermined firing temperature so as to obtain the sensor element 101. The thus obtained sensor element 101 is accommodated into a predetermined housing so as to be incorporated into a main body (not shown in the drawing) of the gas sensor 100 and, thereby, the gas sensor 100 is obtained.

In this regard, the first to third diffusion-controlled portions 11, 13, and 30 can be formed by coating the upper and lower surfaces of the green sheet serving as the spacer layer 5 in the pattern printing with a material to disappear and making this material to disappear during firing. The above-described method for forming the diffusion-controlled portion is known, and is described in, for example, Japanese Patent No. 4911910. Meanwhile, patterns of the side electrode portions 22c, 22d, 51c, and 51d can be formed by, for example, known through hole printing. Specifically, when pattern printing is performed, initially, patterns composed of the electrically conductive paste serving as the side electrode portions 22c, 22d, 51c, and 51d are formed on the upper surface of the green sheet serving as the spacer 5 by screen printing. Subsequently, the lower surface side of the green sheet serving as the spacer 5 is brought into the state under negative pressure, the electrically conductive paste is made to flow into the space serving as the measurement object-gas flow portion and, thereby, portions serving as left and right inner circumferential surfaces of the measurement object-gas flow portion are coated with the electrically conductive paste.

In this regard, an electrically conductive paste, in which, for example, a powder serving as the material for the above-described each electrode is dispersed in a solvent, e.g., acetone, is used for the inside pump electrode 22, the outside pump electrode 23, the reference electrode 42, and the auxiliary pump electrode 51. It is preferable that a sintering aid (binder) or a pore-forming material be added to the electrically conductive paste. Examples of the sintering aid include silicon dioxide and calcium carbonate. Regarding the pore-forming material, a material which disappears during sintering can be used and examples thereof include theobromine and acrylic resins. The particle diameter and the amount of addition of the pore-forming material are adjusted appropriately in accordance with, for example, the porosities of the individual electrodes. Also, the viscosity of the electrically conductive paste is adjusted appropriately in accordance with the thicknesses of the individual electrodes. The electrically conductive paste for the measurement electrode 44 can be adjusted in the same manner as the electrically conductive pastes for the other individual electrodes except that a reduction catalyst (for example, platinum group elements, e.g., ruthenium, rhodium, palladium, osmium, and iridium) for reducing a specific gas (NOx in the present embodiment) is added.

Here, the correspondence between the constituent elements of the present embodiment and the constituent elements of the present invention will be made clear. The layers 1 to 6 of the present embodiment correspond to the laminate, the outside pump electrode 23 corresponds to the outside pump electrode, the inside pump electrode 22 corresponds to the inside main pump electrode, the auxiliary pump electrode 51 corresponds to the inside auxiliary pump electrode, the measurement electrode 44 corresponds to the measurement electrode, and the reference electrode 42 corresponds to the reference electrode.

According to the gas sensor 100 of the present embodiment described above in detail, the sensor element 101 includes the laminate (layers 1 to 6), in which a plurality of oxygen ion-conductive solid electrolyte layers are stacked and in which the measurement object-gas flow portion is disposed so as to introduce the gas to be measured from the outside, the outside pump electrode 23 disposed on the outside surface of the laminate, the inside pump electrode 22 disposed on the inner circumferential surface of the measurement object-gas flow portion, the auxiliary pump electrode 51 disposed on the inner circumferential surface of the measurement object-gas flow portion and disposed on the side downstream from the inside pump electrode 22 in the flow of the gas to be measured, the measurement electrode 44 disposed on the inner circumferential surface of the measurement object-gas flow portion and disposed on the side downstream from the auxiliary pump electrode 51 in the flow of the gas to be measured, and the reference electrode 42, which is disposed in the laminate and to which a reference gas serving as the reference of detection of the specific gas concentration in the gas to be measured, is introduced. Then, the value of the volume ratio Va is 14.5 or more and 51.5 or less and the value of the volume ratio Vb is 5.0 or more and 17.5 or less. Consequently, the controllability of feedback control using a sensor element 101 is improved.

Also, in the case where the value of the volume ratio Va is 22.5 or more and 35.0 or less, the controllability of feedback control is further improved. In the case where the value of the volume ratio Vb is 8.0 or more and 12.0 or less, the controllability of feedback control is further improved. Also, the value of the volume ratio VC is 1.0 or more and 7.0 or less and, thereby, the controllability of feedback control is further improved.

In addition, the laminate has the measurement object-gas flow portion, in which the first internal space 20 and the second internal space 40 are disposed in that order from the inlet of the gas to be measured along the introduction direction, the inside main pump electrode 22 is disposed on the inner circumferential surface of the first internal space 20, the inside auxiliary pump electrode 51 is disposed on the inner circumferential surface of the second internal space 40. Then, the sensor element 101 is configured to include the outside pump electrode 23, the inside pump electrode 22, and the second solid electrolyte layer 6 between the outside pump electrode 23 and the inside pump electrode 22 in the laminate and includes the main pump cell 21 which performs pumping in or pumping out of oxygen of the first internal space 20. Also, the sensor element 101 is configured to include the outside pump electrode 23, the auxiliary pump electrode 51, and the second solid electrolyte layer 6 between the outside pump electrode 23 and the auxiliary pump electrode 51 in the laminate and includes the auxiliary pump cell 50 which performs pumping in or pumping out of oxygen of the second internal space 40. In addition, the sensor element 101 is configured to include the outside pump electrode 23, the measurement electrode 44, and the solid electrolyte layer (second solid electrolyte layer 6, spacer 5, and first solid electrolyte layer 4) between the outside pump electrode 23 and the measurement electrode 44 in the laminate and includes the measurement pump cell 41 which performs pumping in or pumping out of oxygen around the measurement electrode 44.

Incidentally, needless to say, the present invention is not limited to the above-described embodiments and can be executed in various forms within the technical scope of the present invention.

In the above-described embodiment, the inside pump electrode 22 is specified as a tunnel form electrode including the ceiling electrode portion 22a, the bottom electrode portion 22b, and the side electrode portions 22c and 22d but is not limited to the tunnel form. For example, the inside pump electrode 22 may include only the ceiling electrode portion 22a or may include only the bottom electrode portion 22b. Likewise, the auxiliary pump electrode 51 is not limited to the tunnel form.

Figure 3:
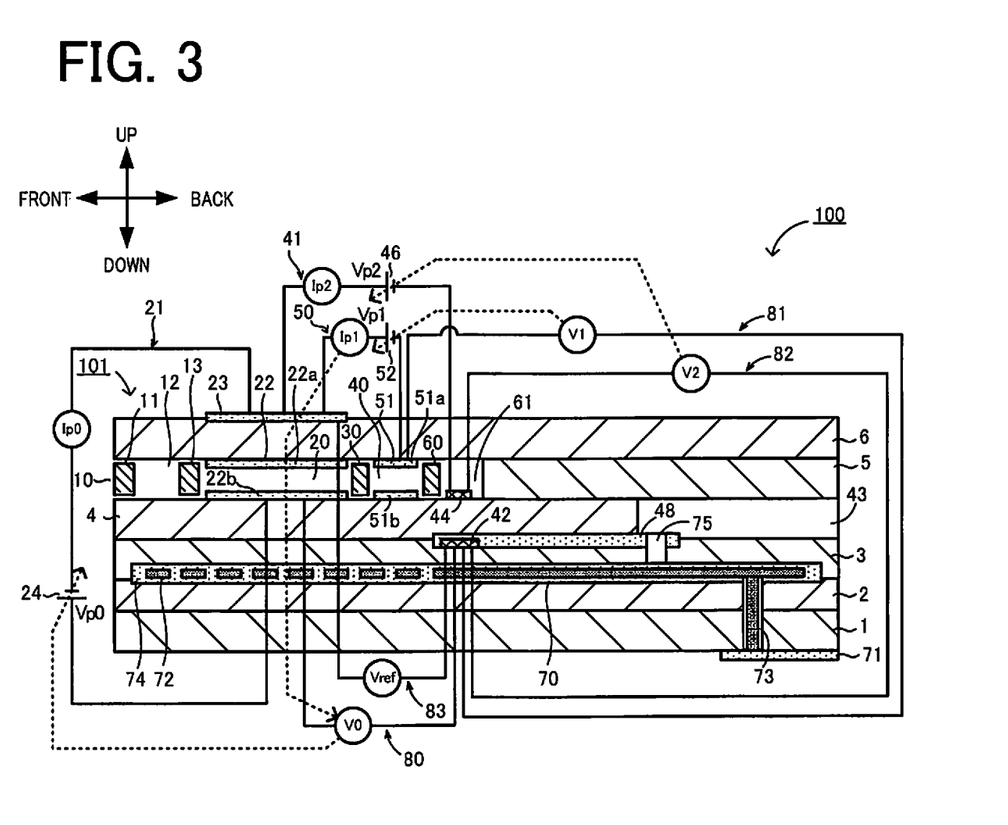
FIG. 3 is a schematic sectional view of a gas sensor 100 of a modified example.

In the above-described embodiment, the sensor element 101 of the gas sensor 100 includes the first internal space 20 and the second internal space 40, although not limited to these. For example, a third internal space may be further included. FIG. 3 is a schematic sectional view of a gas sensor 100 of a modified example in this case. As shown in FIG. 3, in this gas sensor 100 of the modified example, the measurement electrode 44 is not covered with the fourth diffusion-controlled portion 45. Instead, a fourth diffusion-controlled portion 60 as with the third diffusion-controlled portion 30 is disposed between the auxiliary pump electrode 51 and the measurement electrode 44. Consequently, the second internal space 40, the fourth diffusion-controlled portion 60, and a third internal space 61 are disposed so as to adjoin and communicate in that order and constitute part of a measurement object-gas flow portion. Then, the auxiliary pump electrode 51 is disposed in the second internal space 40 and the measurement electrode 44 is disposed on the upper surface of the first solid electrolyte layer 4 facing the third internal space 61. This gas sensor 100 of the modified example can detect the NOx concentration in the gas to be measured as in the above-described embodiment because the fourth diffusion-controlled portion 60 has the same function as the fourth diffusion-controlled portion 45 shown in FIG. 1. Consequently, the controllability of feedback control is improved by adjusting the volume ratio VA and the volume ratio Vb as in the above-described embodiment.

In the above-described embodiment, the reference electrode 42 is disposed directly on the upper surface of the third substrate layer 3, although not limited to this. For example, the reference electrode 42 may be disposed directly on the lower surface of the first solid electrolyte layer 4.

In the above-described embodiment, the sensor element 101 may be provided with a porous protective film covering the surfaces (for example, upper, lower, left, and right surfaces and front surface) on the front end side of the solid electrolyte layer. A porous protective layer 91 may be composed of a porous body, e.g., an alumina porous body, a zirconia porous body, a spinel porous body, a cordierite porous body, a titania porous body, or a magnesia porous body.

The above-described embodiment shows the gas sensor 100 provided with the variable power supplies 24, 46, and 52 and the like as a specific example of the sensor element according to the present invention. However, the sensor element according to the present invention may be specified as a simple sensor element 101 without configurations, such as the variable power supplies 24, 46, and 52, external wiring, and the like.

In the above-described embodiment, the gas inlet 10 is disposed in the front end surface of the sensor element 101 but is not limited to the front end surface as long as the gas to be measured can be introduced from the outside. For example, the gas inlet 10 may be disposed in the upper surface (upper surface of the second solid electrolyte layer 6) of the sensor element 101.

EXAMPLES

Specific production example of the sensor elements will be described below as examples. Experimental examples 3 to 11 and 14 to 17 correspond to the examples of the present invention, and Experimental examples 1, 2, 12, and 13 correspond to the comparative examples. In this regard, the present invention is not limited to the examples below.

Experimental examples 1 to 13

In Experimental examples 1 to 13, gas sensors 100 including the sensor element 101 shown in FIGS. 1 and 2 were formed following the method for manufacturing the gas sensor 100 of the above-described embodiment. Experimental examples 1 to 13 had the same configuration except that the volume ratios Va, Vb, and Vc were variously changed as shown in Table 1 below. Regarding the size of the sensor element 101, the length in the forward or backward direction was 67.5 mm, the width in the lateral direction was 4.25 mm, and the thickness in the vertical direction was 1.45 mm. In experimental examples 1 to 13, the volume Vm was adjusted within the range of 0.3 mm$^3$ to 2.0 mm$^3$, the volume Vs was adjusted within the range of 0.1 mm$^3$ to 0.6 mm$^3$, and the volume Vr was adjusted within the range of 0.01 mm$^3$ to 0.03 mm$^3$. Each of the volumes Vm, Vs, and Vr was adjusted by changing the thickness of the electrode. In this regard, when producing the sensor element main body 101a, ceramic green sheets were prepared by mixing zirconia particles containing 4 percent by mole of yttria serving as a stabilizer, an organic binder, and an organic solvent and performing tape forming. The electrically conductive paste for the inside pump electrode 22, the outside pump electrode 23, the reference electrode 42, and the auxiliary pump electrode 51 was adjusted as described below. A premixed liquid was obtained by adding predetermined amounts of Pt containing 1 percent by mass of Au, a pore-forming material (theobromine) having a particle diameter of 1.0 μm, and acetone serving as a solvent to zirconia particles containing 4 percent by mole of yttria serving as a stabilizer and performing premixing. An organic binder solution obtained by dissolving 20 percent by mass of polyvinylbutyral into 80 percent by mass of butyl carbitol was added to the premixed liquid in such a way that the proportion relative to a total volume of yttria partially stabilized zirconia and pore-forming material in the premixed liquid became 50 percent by volume, mixing was performed and, thereafter, the viscosity was adjusted by adding butyl carbitol appropriately so as to obtain the electrically conductive paste. The electrically conductive paste for the measurement electrode 44 was obtained in the same manner as that for the other electrodes except that 30 percent by mass of Rh powder having a particle diameter of 2.0 μm was further added.

Evaluation Test

Regarding Experimental examples 1 to 13, the controllability of feedback control was evaluated. Specifically, the measurement was performed as described below. Initially, the gas sensor 100 of each of Experimental examples 1 to 13 was attached to an exhaust gas pipe of an automobile. Subsequently, the heater 72 was energized so as to heat the sensor element 101 at a temperature of 800° C. In this state, the feedback control explained in the above-described embodiment was started. Thereafter, the gasoline engine of the automobile was operated under predetermined operating conditions (the number of revolutions of the engine of 4,000 rpm, gauge pressure of the exhaust gas of 20 kPa, and the λ value of 0.83). Then, changes in the electromotive forces V0, V1, and V2 with a lapse of time from the start of operation of the engine were continuously measured, and the measurement values were compared with the target values V0*, V1*, and V2*. Subsequently, the controllability of the measurement value relative to the target value was evaluated. Specifically, in the case where all the times T elapsed until the measurement values of the electromotive forces V0, V1, and V2 converged within ±10% of the target values were 2.0 seconds or less, the controllability was rated as very good (⊚). Also, in the case where all the times T of the electromotive forces V0, V1, and V2 were 3.0 seconds or less, the controllability was rated as good (○). In the case where at least one of the times T of the electromotive forces V0, V1, and V2 was more than 3.0 seconds, the controllability was rated as poor (x). The evaluation results are shown in Table 1.

TABLE 1

|  | Experimental Example 1 | Experimental Example 2 | Experimental Example 3 | Experimental Example 4 | Experimental Example 5 | Experimental Example 6 | Experimental Example 7 |
|---|---|---|---|---|---|---|---|
| Volume Ratio Va ※1 | 9.39 | 14.08 | 17.84 | 19.43 | 22.25 | 23.75 | 28.16 |
| Volume Ratio Vb ※2 | 3.22 | 4.83 | 6.12 | 6.67 | 7.63 | 8.15 | 9.66 |
| Volume Ratio Vc ※3 | 2.92 | 2.92 | 2.92 | 2.92 | 2.92 | 2.92 | 2.92 |
| Controllability | X | X | ○ | ○ | ○ | ⊚ | ⊚ |

|  | Experimental Example 8 | Experimental Example 9 | Experimental Example 10 | Experimental Example 11 | Experimental Example 12 | Experimental Example 13 |
|---|---|---|---|---|---|---|
| Volume Ratio Va ※1 | 30.32 | 35.01 | 44.68 | 47.88 | 51.63 | 56.32 |
| Volume Ratio Vb ※2 | 10.40 | 12.01 | 15.33 | 16.10 | 17.71 | 19.32 |
| Volume Ratio Vc ※3 | 2.92 | 2.92 | 2.92 | 2.97 | 2.92 | 2.92 |
| Controllability | ⊚ | ○ | ○ | ○ | X | X |

※1 Volume Ratio Va = (Volume Vm of Inside Pump Electrode 22)/(Volume Vr of Measurement Electrode 44)
※2 Volume Ratio Vb = (Volume Vs of Auxiliary Pump Electrode 51)/(Volume Vr of Measurement Electrode 44)
※3 Volume Ratio Vc = (Volume Vm of Inside Pump Electrode 22)/(Volume Vs of Auxiliary Pump Electrode 51)

As is clear from Table 1, regarding Experimental examples 3 to 11 in which the values of the volume ratio Va were 14.5 or more and 51.5 or less and, in addition, the values of the volume ratio Vb were 5.0 or more and 17.5 or less, the controllability was good or very good. Also, regarding Experimental examples 6 to 8 in which the values of the volume ratio Va were 22.5 or more and 35.0 or less and, in addition, the values of the volume ratio Vb were 8.0 or more and 12.0 or less, the controllability was very good. Meanwhile, regarding Experimental examples 1 and 2 in which the values of the volume ratio Va were less than 14.5 and, in addition, the values of the volume ratio Vb were less than 5.0, the values of the electromotive forces were not changed easily, that is, the responsiveness was degraded and, therefore, the times T increased. On the other hand, regarding Experimental examples 12 and 13 in which the values of the volume ratio Va were more than 51.5 and, in addition, the values of the volume ratio Vb were more than 17.5, the values of the electromotive forces overshot the target values and, therefore, the times T increased.

From the results shown in Table 1, it is considered that the value of the volume ratio Va needs to be 14.5 or more, and the value is preferably 17.5 or more, more preferably 22.5 or more, and further preferably 23.5 or more. Also, it is considered that the value of the volume ratio Va needs to be 51.5 or less, and the value is preferably 48.0 or less, more preferably 35.0 or less, and further preferably 30.5 or less. Likewise, it is considered that the value of the volume ratio Vb needs to be 5.0 or more, and the value is preferably 6.0 or more and more preferably 8.0 or more. Also, it is considered that the value of the volume ratio Vb needs to be 17.5 or less, and the value is preferably 16.5 or less, more preferably 12.0 or less, and further preferably 10.5 or less.

Experimental Examples 14 to 17

In Experimental examples 14 to 17, gas sensors 100 were formed in the same manner as Experimental example 1 except that the volume ratios Va, Vb, and Vc were variously changed as shown in Table 2 below. In this regard, in Experimental examples 14 to 17, the volume ratios Vc were adjusted to various values different from the values in Experimental examples 1 to 13. In Experimental examples 14 to 17, the volumes WI, Vs, and Vr were adjusted by changing the thickness of the electrode within the above-described ranges in the same manner as in Experimental examples 1 to 13.

Evaluation Test 2

Regarding Experimental examples 14 to 17, the controllability of feedback control was evaluated in the same manner as in Experimental examples 1 to 13. The evaluation results are shown in Table 2.

TABLE 2

|  | Experimental Example 14 | Experimental Example 15 | Experimental Example 16 | Experimental Example 17 |
|---|---|---|---|---|
| Volume Ratio Va ※1 | 15.67 | 20.67 | 34.62 | 46.50 |
| Volume Ratio Vb ※2 | 16.67 | 17.33 | 5.00 | 6.50 |
| Volume Ratio Vc ※3 | 0.94 | 1.19 | 6.92 | 7.15 |
| Controllability | ○ | ○ | ◎ | ○ |

※1 Volume Ratio Va = (Volume Vm of Inside Pump Electrode 22)/(Volume Vr of Measurement Electrode 44)
※2 Volume Ratio Vb = (Volume Vs of Auxiliary Pump Electrode 51)/Volume Vr of Measurement Electrode 44)
※3 Volume Ratio Vc = (Volume Vm of Inside Pump Electrode 22)/(Volume Vs of Auxiliary Pump Electrode 51)

As is clear from Table 2, regarding Experimental examples 14 to 17 in which the values of the volume ratio Va were 14.5 or more and 51.5 or less and, in addition, the values of the volume ratio Vb were 5.0 or more and 17.5 or less, the controllability was good or very good, even though the values of the volume ratio Vc were different from those in Experimental examples 1 to 13. Also, regarding Experimental example 16 in which the value of the volume ratio VA was 22.5 or more and 35.0 or less, the controllability was very good.

The present application claims priority from Japanese Patent Application No. 2015-044293 filed on Mar. 6, 2015, all the contents of Description, Claims, and Drawings of which are incorporated herein by reference.

What is claimed is:

1. A sensor element comprising:
    a laminate, in which a plurality of oxygen ion-conductive solid electrolyte layers are stacked and in which a measurement object-gas flow portion is disposed so as to introduce a gas to be measured from outside of the laminate;
    an outside pump electrode disposed on an outer surface of the laminate;
    an inside main pump electrode disposed on an inner circumferential surface of the measurement object-gas flow portion;
    an inside auxiliary pump electrode disposed on the inner circumferential surface of the measurement object-gas flow portion and disposed on a side downstream from the inside main pump electrode in a flow direction of the gas to be measured;
    a measurement electrode disposed on the inner circumferential surface of the measurement object-gas flow portion and disposed on the side downstream from the inside auxiliary pump electrode in the flow direction of the gas to be measured; and
    a reference electrode disposed within the laminate and to which a reference gas serving as a reference of detection of a specific gas concentration in the gas to be measured is introduced, wherein:
    a value of the volume ratio Va (=Vm/Vr) is 14.5 or more and 51.5 or less and a value of the volume ratio Vb (=Vs/Vr) is 5.0 or more and 17.5 or less, where Vm is a volume of the inside main pump electrode, Vs is a volume of the inside auxiliary pump electrode, and Vr is a volume of the measurement electrode,
    the volume Vm ranges from 0.3 $mm^3$ to 2.0 $mm^3$,
    the volume Vs ranges from 0.1 $mm^3$ to 0.6 $mm^3$, and
    the volume Vr ranges from 0.01 $mm^3$ to 0.03 $mm^3$.

2. The sensor element according to claim 1, wherein the value of the volume ratio Va is 22.5 or more and 35.0 or less.

3. The sensor element according to claim 2, wherein the value of the volume ratio Vb is 8.0 or more and 12.0 or less.

4. The sensor element according to claim 1, wherein the value of the volume ratio Vb is 8.0 or more and 12.0 or less.

5. The sensor element according to claim 1, wherein a value of the volume ratio Vc (=Vm/Vs) is 1.0 or more and 7.0 or less.

6. The sensor element according to claim 1, wherein the laminate has the measurement object-gas flow portion, in which a first internal space and a second internal space are disposed in that order from an inlet of the gas to be measured along the introduction direction,
    the inside main pump electrode is disposed on the inner circumferential surface of the first internal space,
    the inside auxiliary pump electrode is disposed on the inner circumferential surface of the second internal space, and
    a main pump cell which is configured to include the outside pump electrode, the inside main pump electrode, and the solid electrolyte layer between the outside pump electrode and the inside main pump electrode in the laminate and which performs pumping in or pumping out of oxygen of the first internal space,
    an auxiliary pump cell which is configured to include the outside pump electrode, the inside auxiliary pump electrode, and the solid electrolyte layer between the outside pump electrode and the inside auxiliary pump electrode in the laminate and which performs pumping in or pumping out of oxygen of the second internal space, and
    a measurement pump cell which is configured to include the outside pump electrode, the measurement electrode, and the solid electrolyte layer between the outside pump electrode and the measurement electrode in the laminate and which performs pumping in or pumping out of oxygen around the measurement electrode are included.

7. A gas sensor comprising the sensor element according to claim 1.

8. A sensor element comprising:

a laminate, in which a plurality of oxygen ion-conductive solid electrolyte layers including a first solid electrolyte layer and a second solid electrolyte layer are stacked and in which a measurement object-gas flow portion is disposed so as to introduce a gas to be measured from outside of the laminate;

an outside pump electrode disposed on an outer surface of the laminate;

an inside main pump electrode disposed on an inner circumferential surface of the measurement object-gas flow portion, the inside main pump electrode including a portion disposed on at least one of a surface of the first solid electrolyte layer and a surface of the second solid electrolyte layer, the inside main pump electrode being located in a first space between the first solid electrolyte layer and the second solid electrolyte layer;

an inside auxiliary pump electrode disposed on the inner circumferential surface of the measurement object-gas flow portion and disposed on a side downstream from the inside main pump electrode in a flow direction of the gas to be measured, the inside auxiliary pump electrode including a portion disposed on at least one of the surface of the first solid electrolyte layer and the surface of the second solid electrolyte layer, the inside auxiliary pump electrode being located in a second space between the first solid electrolyte layer and the second solid electrolyte layer;

a measurement electrode disposed on the inner circumferential surface of the measurement object-gas flow portion and disposed on the side downstream from the inside auxiliary pump electrode in the flow direction of the gas to be measured, the measurement electrode being located in a third space between the first solid electrolyte layer and the second solid electrolyte layer; and a reference electrode disposed within the laminate and to which a reference gas serving as a reference of detection of a specific gas concentration in the gas to be measured is introduced, wherein a value of the volume ratio Va (=Vm/Vr) is 14.5 or more and 51.5 or less and a value of the volume ratio Vb (=Vs/Vr) is 5.0 or more and 17.5 or less, where Vm is a volume of the inside main pump electrode, Vs is a volume of the inside auxiliary pump electrode, and Vr is a volume of the measurement electrode, the volume Vm ranges from 0.3 $mm^3$ to 2.0 $mm^3$, the volume Vs ranges from 0.1 $mm^3$ to 0.6 $mm^3$, and the volume Vr ranges from 0.01 $mm^3$ to 0.03 $mm^3$.

9. The sensor element according to claim 8, wherein the second space and the third space are separated by a diffusion-controlled portion.

* * * * *